(12) United States Patent
Ueno et al.

(10) Patent No.: US 8,389,542 B2
(45) Date of Patent: *Mar. 5, 2013

(54) DOSAGE UNIT COMPRISING A PROSTAGLANDIN ANALOG FOR TREATING CONSTIPATION

(75) Inventors: Ryuji Ueno, Potomac, MD (US); Myra L. Patchen, Fairfax, VA (US)

(73) Assignee: Sucampo AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/330,942

(22) Filed: Dec. 20, 2011

(65) Prior Publication Data

US 2012/0088824 A1    Apr. 12, 2012

Related U.S. Application Data

(62) Division of application No. 10/293,516, filed on Nov. 14, 2002, now Pat. No. 8,097,653.

(60) Provisional application No. 60/331,316, filed on Nov. 14, 2001.

(51) Int. Cl.
- *A61K 31/44* (2006.01)
- *A61K 31/34* (2006.01)
- *A61K 31/19* (2006.01)

(52) U.S. Cl. .................. 514/302; 514/469; 514/573

(58) Field of Classification Search .................. 514/302, 514/469
See application file for complete search history.

(56) References Cited

U.S. PATENT DOCUMENTS

| 4,158,062 A | 6/1979 | Caton et al. |
| 5,117,042 A | 5/1992 | Ueno et al. |

(Continued)

FOREIGN PATENT DOCUMENTS

| EP | 0 310 305 A2 | 4/1989 |
| EP | 0 424 156 A2 | 4/1991 |

(Continued)

OTHER PUBLICATIONS

A. Robert, J.E. Nezamis, C. Lancaster, A.J. Hanchar, and M.S. Klepper, Enteropooling Assay: A Test for Diarrhea Produced by Prostaglandins; Prostaglandins, May 1976, vol. 11, No. 5, 809-828.

(Continued)

*Primary Examiner* — Melenie McCormick
*Assistant Examiner* — Gigi Huang
(74) *Attorney, Agent, or Firm* — Sughrue Mion, PLLC

(57) ABSTRACT

A dosage unit for treating constipation in a human patient is described. The dosage unit of the invention includes a halogenated prostaglandin analog and a pharmaceutically suitable excipient. The dosage unit relieves constipation without substantial side effects. In particular, the dosage unit includes a prostaglandin (PG) analog represented by Formula (I) and/or its tautomers, and a pharmaceutically suitable excipient, wherein the dosage unit contains the PG analog in an amount of 24 μg+/−10%:

Formula (I)

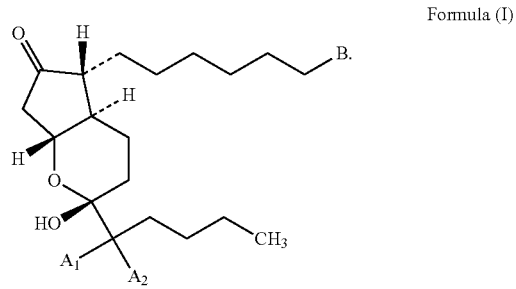

13 Claims, 3 Drawing Sheets

U.S. PATENT DOCUMENTS

| | | | |
|---|---|---|---|
| 5,164,415 | A | 11/1992 | Ueno |
| 5,290,811 | A | 3/1994 | Ueno et al. |
| 5,317,032 | A * | 5/1994 | Ueno et al. ................ 514/530 |
| 5,426,115 | A | 6/1995 | Ueno et al. |
| 5,599,972 | A | 2/1997 | Miyazawa et al. |
| 5,739,161 | A | 4/1998 | Ueno |
| 6,142,485 | A | 11/2000 | Muller et al. |
| 6,197,821 | B1 | 3/2001 | Ueno |
| 6,242,485 | B1 | 6/2001 | Ueno |
| 6,414,016 | B1 | 7/2002 | Ueno |
| 6,492,417 | B1 | 12/2002 | Sharif et al. |
| 6,583,174 | B1 | 6/2003 | Ueno et al. |
| 6,982,283 | B2 | 1/2006 | Ueno |
| 7,064,148 | B2 | 6/2006 | Ueno et al. |
| 8,114,890 | B1 * | 2/2012 | Ueno ........................ 514/300 |
| 2003/0119898 | A1 | 6/2003 | Ueno et al. |
| 2003/0130352 | A1 | 7/2003 | Ueno et al. |
| 2004/0138308 | A1 | 7/2004 | Ueno et al. |

FOREIGN PATENT DOCUMENTS

| | | |
|---|---|---|
| EP | 0 430 551 A2 | 6/1991 |
| EP | 0 430 552 A2 | 6/1991 |
| EP | 0 455 448 A2 | 11/1991 |
| EP | 0 467 564 A2 | 1/1992 |
| EP | 0 503 887 A2 | 9/1992 |
| EP | 0 978 284 A1 | 2/2000 |
| JP | 53-50141 | 5/1978 |
| JP | 2-109 A | 1/1990 |
| JP | 2-32055 A | 2/1990 |
| JP | 4-210631 A | 7/1992 |
| JP | 6-81728 B2 | 10/1994 |
| WO | 01/76593 A2 | 10/2001 |
| WO | WO 02/20007 A1 | 3/2002 |
| WO | 02/094274 A1 | 11/2002 |
| WO | WO 02/089812 A1 | 11/2002 |
| WO | 03/041716 A1 | 5/2003 |
| WO | 03/043639 A2 | 5/2003 |

OTHER PUBLICATIONS

André Robert, Antisecretory, Antiulcer, Cytoprotective and Diarrheogenic Properties of Prostaglandins; Advances in Prostaglandin and Thromboxane Research, vol. 2, 1976, pp. 507-520.

André Robert, Prostaglandins and the Gastrointestinal Tract, Chapter 57, Physiology of the Gastrointestinal Tract, edited by Leonard R. Johnson, Raven Press, New York, 1981, pp. 1407-1434.

C. J. Hawkey and D.S. Rampton; Prostaglandins and the Gastrointestinal Mucosa: Are They Important in Its Function, Disease, or Treatment, Gastroenterology 1985; 89: 1162-88.

Charles E. Eberhart and Raymond N. Dubois; Eicosanoids and the Gastrointestinal Tract, Gastroenterology 1995; 109:285-301.

D.S. Rampton, Prostanoids and intestinal physiology, Biology and Chemistry of Prostaglandins and Related Eicosanoids, pp. 323-344 (Churchill Livingstone, 1988).

Eckhard Beubler, Klaus Bukhave, and Jorgen Rask-Madsen, Significance of Calcium for the Prostaglandin E.sub.2-Meidated Secretory Response to 5-Hydroxytryptamine in the Small Intestine of the Rat In Vivo; Gastroenterology 1986; 90: 1972-7.

Esam A. Dajani, Erika. W. Roge, and Ralph E. Bertermann; Effects of Prostaglandins, Diphenoxylate and Morphine on Intestinal Motility In Vivo; European Journal of Pharmacology, vol. 34, No. 1 (Nov. 1975), pp. 105-113.

I. H. M. Main, Pharmacology of prostaglandins, Postgraduate Medical Journal (1988) 64 (Suppl. 1), 3-6.

J.L. Wallace & A.W. Tigley, Review article: new insights into prostaglandins and mucosal defence; Aliment Pharmacol Ther 1995; 9: 227-235.

J.M. Hunt & E.L. Gerring, The effect of prostaglandin E1 on motility of the equine gut; J. Vet. Pharmacol. Therap. 8, 165-173, 1985.

John F. Johanson, Michele A. Gargano, Myra L. Patchen, and Ryuji Ueno; Efficacy and Safety of a Novel Compound, RU-0211, for the Treatment of Constipation; Gastroenterology, vol. 122, No. 4, Suppl. 1 (Apr. 2002) p. A-315.

Jon P.Monk and Stephen P. Clissold, Misoprostol: A Preliminary Review of Its Pharmacodynamic and Pharmacokinetic Properties, and Therapeutic Efficacy in the Treatment of Peptic Ulcer Disease; Drugs 33: 1-30 (1987) ADIS Press Limited.

Joseph H. Sellin, Intestinal Electrolyte Absorption and Secretion; Pathophysiology, Diagnosis, and Management, pp. 1451-1471 (WB Saunders Company, 1998), Chapter 86.

Koichi Takahashi, Takashi Suzuki, Hitomi Sakano, and Nobuyasu Mizuno, Effect of Vehicles on Diclofenac Permeation across Excised Rat Skin, Biol. Pharm. Bull., vol. 18, No. 4, pp. 571-575 (1995).

L.L. Clarke and R.A. Argenzio, NaCl transport across equine proximal colon and the effect of endogenous prostanoids; American Journal of Physiology, 259: G62-G69, American Physiological Society, 1990.

M. Pairet, T. Bouyssou, and Y. Ruckebusch, Colonic formation for soft feces in rabbits: a role for endogenous prostaglandins; American Journal of Physiology, 250: G302-G308, American Physiological Society, 1986.

Miralax™, Polyethylene Glycol 3350, NF Powder for Solution Package insert, Braintree Laboratories, Inc., TRE-0571, Nov. 2001.

Nathaniel F. Pierce, M.D., Charles C.J. Carpenter, Jr., M.D., Herbert L. Elliott, M.D., and William B. Greenough, III, M.D., Effects of Prostaglandins, Theophylline, and Cholera Exotoxin upon Transmucosal Water and Electrolyte Movement in the Canine Jejunum; Gastroenterology, vol. 60 No. 1 1971 pp. 22-32.

Sanders, Kenton M., Role of prostaglandins in regulating gastric motility; American Journal of Physiology, 247: G117-G126, American Physiological Society, 1984.

The Columbia Encyclopedia, Sixth Edition, tautomer, Nov. 25, 2007, http://www.encyclopedia.com/doc/1E-tautomer.html, 1 page.

Timothy S. Gaginella, Eicosanoid-Mediated Intestinal Secretion; Textbook of Secretory Diarrhea, Raven Press, New York, 1990, pp. 15-30.

ZELNORM® (tegaserod maleate) Package insert, Novartis, T2004-53/T2004-54, 89015305 Aug. 2004, 18 pages.

Cuppoletti John et al.: "Recombinant and native intestinal cell ClC-2 Cl-channels are activated by RU-0211", Gastroenterology, vol. 122, No. 4 Suppl. 1, Apr. 2002, p. A.538, & Digestive Disease Week and the 103rd Annual Meeting of the American Gastroenterological Association; San Francisco, CA, USA; May 19-22, 2002, ISSN:0016-5085.

Dunphy Rebecca C et al: "Drug treatment options for irritable bowel syndrome: Managing for success", Drugs & Aging, ADIS Internation Ltd., NZ, vol. 18, No. 3, Jan. 1, 2001, pp. 201-211.

Extended European Search Report for corresponding Application 10177588.0-2112/2281564 dated Aug. 3, 2012.

Hyams J S: "Functional gastrointestinal disorders", Current Opinion in Pediatrics, Current Science, Philadelphia, PA, US, vol. 11, No. 5, Jan. 1, 1999, pp. 375-378.

Johanson J F et al: "Efficacy and Safety of a Novel Compound, RU-0211, for the Treatment of Constipation", Gastroenterology, W.B. Saunders Company, Philadelphia, US, vol. 122, No. 4, Suppl 1, Apr. 2002, p. A315.

Locke G R: "The epidemiology of functional gastrointestinal disorders in North America". Gastroenterology Clinics of North America, vol. 25, No. 1, Mar. 1, 1996, pp. 1-19.

* cited by examiner

DOSAGE UNIT COMPRISING A PROSTAGLANDIN ANALOG FOR TREATING CONSTIPATION

CROSS REFERENCE TO RELATED APPLICATIONS

This application is a divisional application of application Ser. No. 10/293,516 filed Nov. 14, 2002, which claims benefit to Provisional Application No. 60/331,316 filed Nov. 14, 2001, the disclosures of all of which are incorporated herein by reference.

TECHNICAL FIELD

The present invention relates to a novel dosage unit of a halogenated prostaglandin analog for the treatment and prevention of constipation in human patients.

BACKGROUND ART

Constipation is generally defined as infrequent and difficult passage of stool. Medical reporting estimates that one of every 50 people in the United States suffers from constipation, making it one of the most common disorders among Americans. Constipation is more likely to affect females than males and more likely to occur in older adults, showing an exponential increase after the age of 65. The actual occurrence of constipation is likely higher than reported, as many individuals suffer at home without seeking professional care.

Although in some instances constipation may be caused by obstruction, most constipation can be associated with factors such as a diet low in soluble and insoluble fibers, inadequate exercise, medication use (in particular, opiate analgesics, anticholinergic antidepressants, antihistamines, and vinca alkaloids), bowel disorders, neuromuscular disorders, metabolic disorders, poor abdominal pressure or muscular atony.

A precise quantitative definition of constipation has been difficult to establish due to the wide range of perceived "normal" bowel habits, as well as the diverse array of symptoms and signs associated with constipation. The FDA has recognized a need for prescriptive treatment of occasional constipation.

Prostaglandins (hereinafter, referred to as PGs) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

(A)

PGs are classified into several types according to the structure and substituents on the five-membered ring, for example, Prostaglandins of the A series (PGAs);

Prostaglandins of the B series (PGBs);

Prostaglandins of the C series (PGCs);

Prostaglandins of the D series (PGDs);

Prostaglandins of the E series (PGEs);

Prostaglandins of the F series (PGFs);

and the like. Further, they are classified into $PG_1$s containing a 13,14-double bond; $PG_2$s containing, 5,6- and 13,14-double bonds; and $PG_3$s containing 5,6-, 13,14- and 17,18-double bonds. PGs are known to have various pharmacological and physiological activities, for example, vasodilatation, inducing of inflammation, platelet aggregation, stimulating uterine muscle, stimulating intestinal muscle, anti-ulcer effect and the like. The major prostaglandins produced in the human gastrointestinal (GI) system are those of the E, I and F series (Sellin, Gastrointestinal and Liver Disease: Pathophysiology, Diagnosis, and Management. (WB Saunders Company, 1998); Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Hawkey, et al., *Gastroenterology*, 89: 1162-1188 (1985); Eberhart, et al., *Gastroenterology*, 109: 285-301 (1995)).

Under normal physiological conditions, endogenously produced prostaglandins play a major role in maintaining GI function, including regulation of intestinal motility and transit, and regulation of fecal consistency. (Sellin, Gastrointestinal and Liver Disease: Pathophysiology, Diagnosis, and Management. (WB Saunders Company, 1998); Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Hawkey, et al., *Gastroenterology*, 89: 1162-1188 (1985); Eberhart, et al., *Gastroenterology*, 109: 285-301 (1995); Robert, *Adv Prostaglandin Thromboxane Res*, 2:507-520 (1976); Main, et al., *Postgrad Med J*, 64 Suppl 1: 3-6 (1988); Sanders, *Am J Physiol*, 247: G117 (1984); Pairet, et al., *Am J Physiol.*, 250 (3 pt 1): G302-G308 (1986); Gaginella, Textbook of Secretory Diarrhea 15-30 (Raven Press, 1990)). When administered in pharmacological doses, both $PGE_2$ and $PGF_{2\alpha}$ have been shown to stimulate intestinal transit and to cause diarrhea (Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Robert, *Adv Prostaglandin Thromboxane Res*, 2:507-520 (1976)). Furthermore, the most commonly reported side effect of misoprostol, a $PGE_1$ analogue developed for the treatment of peptic ulcer disease, is diarrhea (Monk, et al., Drugs 33 (1): 1-30 (1997)).

PGE or PGF can stimulate the intestines and cause intestinal contraction, but the enteropooling effect is poor. Accordingly, it is impossible to use PGEs or PGFs as cathartics because of side effects such as stomachache caused by the intestinal contraction.

Multiple mechanisms, including modifying enteric nerve responses, altering smooth muscle contraction, stimulating mucous secretion, stimulating cellular ionic (in particular electrogenic Cl⁻ transport) and increasing intestinal fluid volume have been reported to contribute to the GI effects of prostaglandins (Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Hawkey, et al., *Gastroenterology*, 89: 1162-1188 (1985); Eberhart, et al., Gastroenterology, 109: 285-301 (1995); Robert, *Adv Prostaglandin Thromboxane Res*, 2:507-520 (1976); Main, et al., Postgrad Med J, 64 Suppl 1: 3-6 (1988); Sanders, *Am J Physiol*, 247: G117 (1984); Pairet, et al., *Am J Physiol*, 250 (3 pt 1): G302-G308 (1986); Gaginella, Textbook of Secretory Diarrhea 15-30 (Raven Press, 1990); Federal Register Vol. 50, No. 10 (GPO, 1985); Pierce, et al., *Gastroenterology* 60 (1): 22-32 (1971); Beubler, et al., *Gastroenterology*, 90: 1972 (1986); Clarke, et al., *Am J Physiol* 259: G62 (1990); Hunt, et al., *J Vet Pharmacol Ther*, 8 (2): 165-173 (1985); Dajani, et al., *Eur J Pharmacol*, 34(1): 105-113 (1975); Sellin, Gastrointestinal and Liver Disease: Pathophysiology, Diagnosis, and Management 1451-1471 (WB Saunders Company, 1998)). Prostaglandins have additionally been shown to have cytoprotective effects (Sellin, Gastrointestinal and Liver Disease: Pathophysiology, Diagnosis, and Management. (WB Saunders Company, 1998); Robert, *Physiology of the Gastrointestinal Tract* 1407-1434 (Raven, 1981); Robert, *Adv Prostaglandin Thromboxane Res* 2:507-520 (1976); Wallace, et al., Aiiment Pharmacol Ther 9: 227-235 (1995)).

U.S. Pat. No. 5,317,032 to Ueno et al. describes prostaglandin analog cathartics, including the existence of bicyclic tautomers and U.S. Pat. No. 6,414,016 to Ueno describes the bicyclic tautomers as having pronounced activity as anti-constipation agents. The bicyclic tautomers, substituted by one or more halogen atoms can be employed in small doses for relieving constipation. At the C-16 position, especially, fluorine atoms, can be employed in small doses for relieving constipation. The doses, however, by which these prostaglandin analogs are optimally effective is not known. Moreover, the range at which the PG analogs are safe, while yet exerting therapeutic effects, needs to be determined. Clinical dose-ranging studies will be necessary to evaluate the safety and tolerance of PG analogs.

DISCLOSURE OF INVENTION

It is therefore an object of this invention to provide a dosage formulation and a workable, therapeutic approach for relieving and preventing constipation in human patients.

That is, the present invention provides a dosage unit for use in relieving or preventing constipation in a human patient comprising (i) a prostaglandin (PG) analog represented by Formula (I) and/or its tautomer in the range of about 6-96 μg:

Formula (I)

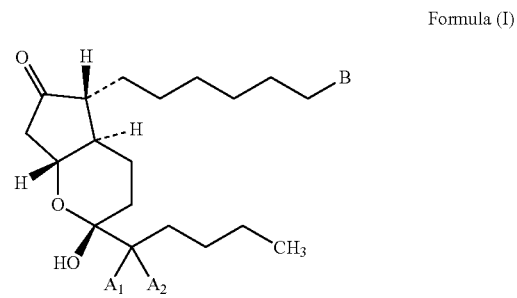

where $A_1$ and $A_2$ are the same or different halogen atoms and

B is —COOH, including its pharmaceutically acceptable salts, esters or amides; and (ii) a pharmaceutically suitable excipient.

Another object of the present invention is to provide a method for treating constipation in a human patient. Accordingly, the instant invention also provides a method for relieving or preventing constipation in a human patient that comprises administering to the patient a dosage unit comprising (i) a PG analog, represented by Formula (I) and/or its tautomer in the range of about 6-96 μg:

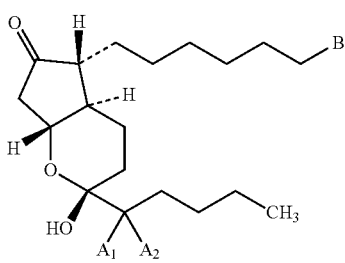

Formula (I)

where $A_1$ and $A_2$ are the same or different halogen atoms and

B is —COOH, including its pharmaceutically acceptable salts, esters or amides; and (ii) a pharmaceutically suitable excipient.

According to the invention, the halogenated PG analog of formula (I) is preferably halogenated with fluorine atoms, to have a cathartic effect. The dosage unit of the invention comprises the PG analog of formula (I) and/or its tautomer in the range of about 6-96 µg per unit. A total daily dose of about 24-72 µg is also preferred. For example, the preferable total daily dose of the PG analog is about 48 µg.

According to the invention, the pharmaceutical excipient may preferably be a medium chain fatty acid to provide a dosage unit is administered orally.

In the graph, [ ]=statistically significant overall p-value based on a Cochran-Mantel Haenszel (CMH) test using modified ridit scores, controlling for site, and using Shaffer's modified sequentially rejective multiple test procedure. *=statistically significant pairwise comparison based on a Cochran-Mantel Haenszel (CMH) test comparing placebo to active drug using modified ridit scores, controlling for site and using Shaffer's modified sequentially rejective multiple test procedure.

Figure 1:
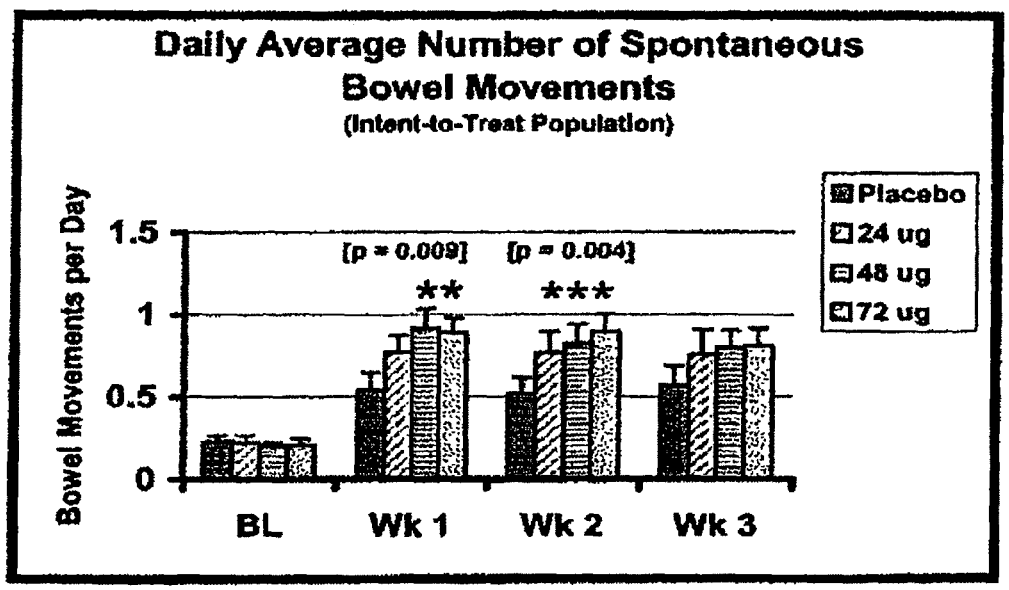
FIG. 1. Graph of daily average number of spontaneous bowel movements in the intent-to-treat population. Daily bowel movements were assessed for the 0 µg, 24 µg, 48 µg and 72 µg doses of Compound A during 0, 1, 2 and 3 weeks of medicating.
Figure 2:
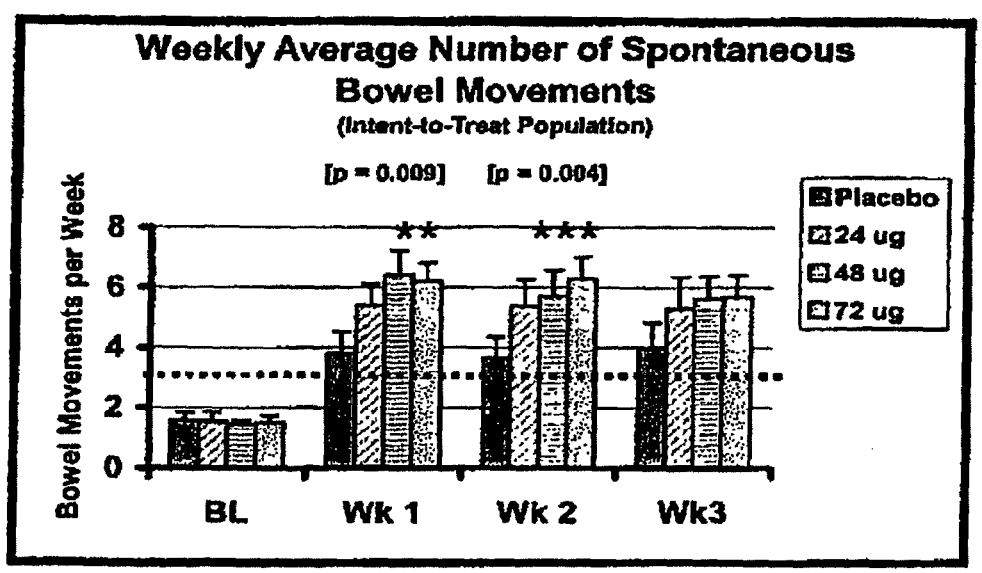

FIG. 2. Graph of weekly average number of spontaneous bowel movements in the intent-to-treat population. Average number of bowel movements were compared across the different treatment groups during 0 weeks, week 1, week 2 and week 3.

In the graph, [ ]=statistically significant overall p-value based on a Cochran-Mantel Haenszel (CMH) test using modified ridit scores, controlling for site, and using Shaffer's modified sequentially rejective multiple test procedure. *=statistically significant pairwise comparison based on a Cochran-Mantel Haenszel (CMH) test comparing placebo to active drug using modified ridit scores, controlling for site and using Shaffer's modified sequentially rejective multiple test procedure. Dotted line represents the cut-line for constipation defined as <3 spontaneous bowel movements per week.

Figure 3:
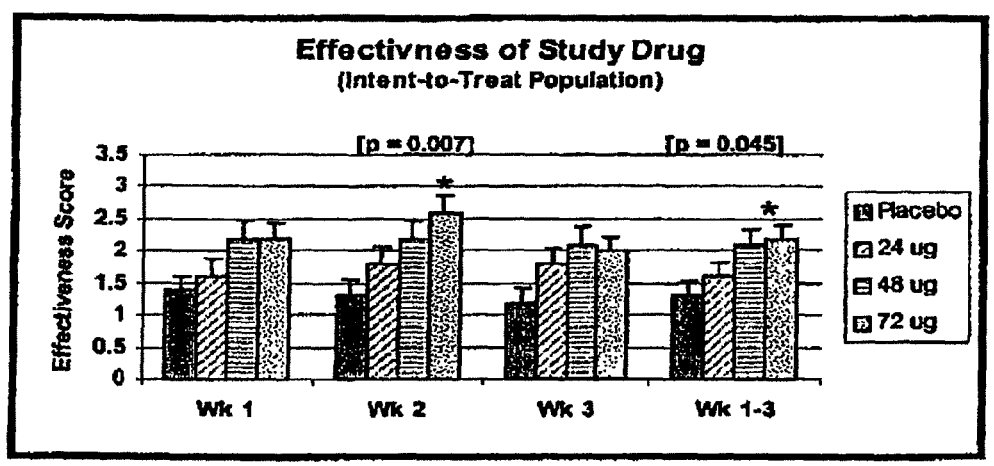

FIG. 3. Graph of study drug effectiveness in the intent-to-treat population. Effectiveness of study drug for the different treatment groups was rated on a scale of 0-4, 4 being the most effective.

In the graph, [ ]=statistically significant overall p-value based on a Cochran-Mantel Haenszel (CMH) test using modified ridit scores, controlling for site, and using Shaffer's modified sequentially rejective multiple test procedure. *=statistically significant pairwise comparison based on a Cochran-Mantel Haenszel (CMH) test comparing placebo to active drug using modified ridit scores, controlling for site and using Shaffer's modified sequentially rejective multiple test procedure. Rating scale: 0=not at all effective, 1=a little bit effective, 2=moderately effective, 3=quite a bit effective and 4=extremely effective.

DETAILED DESCRIPTION OF THE INVENTION

The present invention provides a dosage unit for an anti-constipation composition comprising a halogenated prostaglandin analog as an active ingredient.

Cathartics are thought to work by the combination of one or more mechanisms to increase the water content of feces and promote transfer of the content in the intestines. Halogenated prostaglandin analogs of formula (I) appear to alleviate constipation by mainly acting on the intestinal mucosa to affect the transfer of electrolytes and water from intestinal walls into blood vessels and/or from blood vessels into intestines. These results in reduced water absorption and/or increased water secretion through intestines, increased intraintestinal water pool and transfer of the intraintestinal content.

The present inventors have discovered a dosage regimen and suitable formulations of halogenated prostaglandin analogs for the treatment and prevention of constipation. A dosage unit comprising a PG analog and a pharmaceutically suitable excipient is described herein.

Preparing a Dosage Unit

The dosage unit comprises a prostaglandin analog of formula (I) and a pharmaceutically suitable excipient. The amount of the PG analog present in the dosage unit typically is in the range of about 6-96 µg. As used herein, the term "about" when used in conjunction with a unit of measure can be defined as +/−30% and +/−20%, preferably +/−10%. For example, the range of about 6-96 µg preferably means the range of 5.4-105.6 µg. The preferred dose is in the range of about 24-72 µg. In a more preferred embodiment, the dose is in the range of about 24-60 µg. For example, the dose of said halogenated composition can be about 48 µg. The dosage unit of the invention can be used for constipation treatment and prevention remedies for humans.

(i) PG Analogs

The PG analog, in the present invention is represented by formula (I):

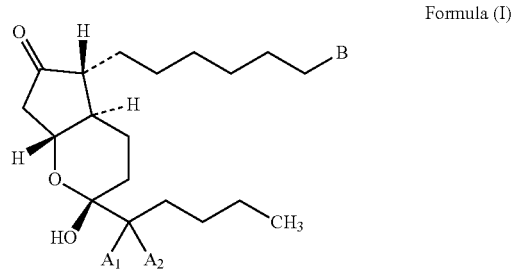

Formula (I)

where $A_1$ and $A_2$ are halogen atoms and B is —COOH, its pharmaceutically acceptable salt, ester or amide.

The term "halogen" is used conventionally to include fluorine, chlorine, bromine, and iodine atoms. Particularly preferable halogen atoms for $A_1$ and $A_2$ are fluorine atoms.

The halogenated PG analog of formula (I) used in the present invention may be an amide, a salt or an ester. Such salts include pharmaceutically acceptable salts, for example, those of alkali metals such as sodium and potassium; those of alkaline earth metals such as calcium and magnesium; those of physiologically acceptable ammonium salts such as ammonia, methylamine, dimethylamine, cyclopetylamine, cylohexylamine, benzylamine, peperidine, ethylenediamine, monoethanolamine, diethanolamine, triethanolamine, monomethylmonoethanolamine, tromethamine, lysine, procaine, caffeine, arginine and tetralkylammonium salt, and the like. These salts may be prepared by a conventional process, for example, from the corresponding acid and base or by salt interchange.

Such esters include, for example, straight or branched alkyl esters, which may contain one or more unsaturated bonds such as methyl, ethyl, propyl, butyl, isopropyl, isobutyl, t-butyl, pentyl and 2-ethylhexyl.

Preferred amides are methyl, ethyl, propyl, isopropyl and butyl amides.

In a preferred embodiment, the dosage unit comprises a PG analog of formula (I) in which $A_1$ and $A_2$ are fluorine atoms. Still more preferred is the one in which B is —COOH.

A dosage unit, as defined herein, is a unit of halogenated PG analog to be administered. Single or multiple dosage units may be administered, making up the dose, a quantity of halogenated PG analog that produces the desired cathartic effect.

The active agent of this invention exists as a bicyclic compound in a solid state, but partially forms a tautomer of the above compound when dissolved in a solvent. In the absence of water, compounds represented by formula (I) exist predominantly in the form of the bicyclic compound. In aqueous media, it is believed that hydrogen bonding occurs between, for example, the ketone position at the C-15 position, thereby hindering bicyclic ring formation. In addition, it is believed that the halogen atoms at the C-16 position promote bicyclic ring formation. The tautomerism between the hydroxy at the C-11 position and the keto moiety at the C-15 position, shown below, is especially significant in the case of compounds having a 13,14 single bond and two fluorine atoms the C-16 position.

Accordingly, the dosage unit of the present invention may comprise isomers of the halogenated PG analog compounds. For example, mono-cyclic tautomers having a keto group at the C-15 position and halogen atoms at the C-16 position.

able excipient may be, therefore, selected depending on the desired form of the dosage unit. According to the invention, "pharmaceutically suitable excipient" means an inert substance, which is suitable for the form, combined with the active ingredient of the invention.

For example, solid composition for oral administration of the present invention may include tablets, preparations, granules and the like. In such a solid composition, one or more active ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the usual work-up, the composition may contain additives other than inactive diluent, for example, lubricant such as magnesium stearate; disintegrant such as fibrous calcium gluconate; stabilizer such as cyclodextrin, for example, α,β- or γ-cyclodextrin; etherified cyclodextrin such as dimethyl-α-, dimethyl-β-, trimethyl-β-, or hydroxypropyl-β-cyclodextrin; branched cyclodextrin such as glucosyl-, maltosyl-cyclodextrin; formylated cyclodextrin, cyclodextrin containing sulfur; phospholipid and the like. When the above cyclodextrins are used, inclusion compound with cyclodextrins may be sometimes formed to enhance stability. Alternatively, phospholipid may be sometimes used to form liposome, resulting in enhanced stability.

Tablets or pills may be coated with film soluble in the stomach or intestine such as sugar, gelatin, hydroxypropyl cellulose, hydroxypropylmethyl cellulose phthalate as needed. Further, they may be formed as capsules with absorbable substances such as gelatins. Preferably, the dosage unit is formulated in a soft gelatin capsule with liquid contents of the halogenated PG analog and a medium chain fatty acid triglyceride. Examples of the medium chain fatty acid triglyceride used in the present invention include a triglyceride of a saturated or unsaturated fatty acid having 6-14 carbon atoms which may have a branched chain. A preferred fatty acid is a straight chain saturated fatty acid, for example caproic acide (C6), caprylic acid (C8), capric acid (C10), lauric acid (C12) and myristic acid (C14). In addition, two or more medium chain fatty acid triglycerides may be used in combination. Further suitable excipients are disclosed in the published PCT application WO 01/27099.

A liquid composition for oral administration may be pharmaceutically acceptable emulsion, solution, suspension, syrup, elixir, as well as generally used inactive diluent. Such

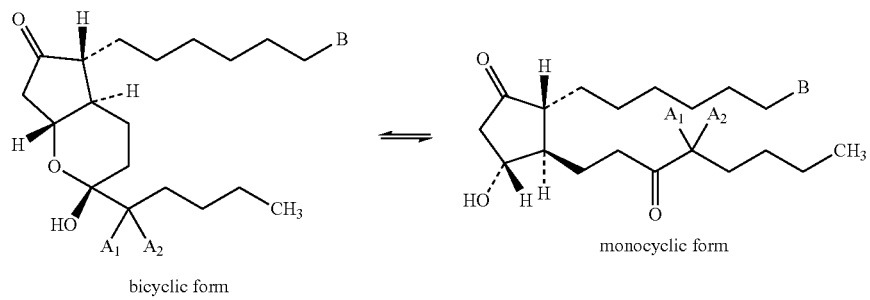

bicyclic form　　　　　　　　　monocyclic form

A preferred compound according to the invention in its monocyclic form can be named as 13,14-dihydro-15-keto-16,16-difluoro-$PGE_1$, according to conventional prostaglandin nomenclature.

(ii) The Pharmaceutically Suitable Excipient

According to the invention, the dosage unit of the invention may be formulated in any form. The pharmaceutically suitcomposition may contain, in addition to the inactive diluent, adjuvants such as lubricants and suspensions, sweetening agents, flavoring agents, preservatives, solubilizers, anti-oxidants and the like. The details of the additives may be selected from those described in any general textbooks in the pharmaceutical field. Such liquid compositions may be directly enclosed in soft capsules. Solutions for parenteral administration, for example, suppository, enema and the like according to the present invention include sterile, aqueous or non-aqueous solution, suspension, emulsion, detergent and the like. The aqueous solution and suspension includes, for example, distilled water, physiological saline and Ringer's solution.

The non-aqueous solution and suspension include, for example, propylene glycol, polyethylene glycol, fatty acid triglyceride, vegetable oil such as olive oil, alcohols such as ethanol, polysorbate and the like. Such composition may contain adjuvants such as preservatives, wetting agent, emulsifier, dispersant, anti-oxidants and the like.

The dosage unit of the present invention is parenterally acceptable, however orally is preferred. The test substance is preferably dissolved in Panacet 800 (medium chain fatty acid triglyceride manufactured by Nippon Oil & Fat Co., Ltd., Amagasaki, Japan) and filled in a capsule (each capsule contains 200 µL of the mixture).

A Method for Treating Constipation

The invention further provides a method for relieving or preventing constipation in a human patient that comprises administering to the patient a dosage unit comprising (i) a PG analog represented by Formula (I) or its tautomers in the range of about 6-96 µg:

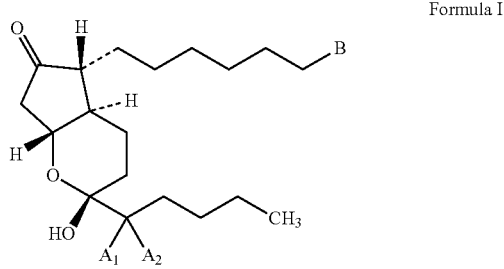

Formula I and (ii) a pharmaceutically suitable excipient. $A_1$ and $A_2$ of the PG analog represented by Formula (I) are halogen atoms and B is —COOH, its pharmaceutically acceptable salt, ester or amide. Preferably, the halogen atoms are fluorine atoms.

According to the method of the invention, the dosage unit of the present invention can be administered systemically or locally by means of oral or parental administration, including a suppository, enema and the like. Single or multiple dosage units may be administered to achieve the desired dose.

Preferably, the total daily dose of the PG analog is in the range of about 24-72 µg. Also preferable, the total daily dose of the PG analog is in the range of about 24-60 µg. Still more preferably, the total daily dose of the PG analog is about 48 µg. The dose may vary somewhat, at the discretion of the physician, depending the age and weight of the patient, conditions, therapeutic effect, administration route, treatment time and the like.

EXAMPLES

The following examples illustrate the present invention but are not in any way intended to limit the scope of this invention. The following abbreviations are used in the examples below:
AE Adverse Event
ITT Intent To Treat
PO Per Os (Orally)
PP Per Protocol
SE Safety Evaluable All randomized patients who took at least one dose of double-blind study medication constituted the safety evaluable (SE) population. These patients were included in the demographic data, baseline characteristic data and safety analysis. For efficacy, the same data set was used and is referred to as the intent-to-treat (ITT) population. Patients who did not comply with the treatment regimen or who took disallowed concomitant medication were considered protocol violators. Key efficacy analyses were also performed on the per-protocol (PP) population, which excluded all data for the affected weeks for protocol violators. Patients whose treatments were adjusted were analyzed in their original treatment group (i.e., as randomized).

Example 1

Phase I Dosage Studies

The safety and tolerance of oral Compound A (13,14-dihydro-15-keto-16,16-difluoro-$PGE_1$) was evaluated in 16 volunteers in a single-dose Phase I study (Phase Ia) at rising per-person doses of 6 µg, 12 µg, 24 µg, 48 µg, 72 µg, and 96 µg compared and in 24 volunteers in a multiple-dose Phase I study (Phase Ib) at rising per-person doses of 24 µg, 30 µg, and 36 µg of Compound A administered three times a day (TID) (i.e., total daily per person doses of 72 µg, 90 µg and 108 µg) for 6 days.

The dose-limiting toxicity in the Phase I studies was nausea. The maximum tolerated single per-person dose of Compound A was 96 µg and the maximum tolerated multiple per-person dose of Compound A was 36 µg taken TID (i.e., a 108 µg total daily dose).

Single Rising Dose Study

96 µg was the maximum tolerated single oral Compound A dose. In the Phase Ia study, serious adverse events (SAE) did not occur at any dose level, but there were a total of 49 AEs. These occurred in 13 of the 17 volunteers and all resolved. Volunteers receiving placebo experienced five AEs. Most AEs could be categorized as either responses or events commonly reported in Phase I clinical trials (such as headache and lightheadedness) or expected pharmacodynamic responses of Compound A (such as loose bowel movements, diarrhea and abdominal cramping).

The number of adverse events increased with dose. The increase in frequency and severity of AEs found between the first four dose increments and the final two dose increments, coupled with the further increase in AEs between the final two dose increments, suggested that 96 µg was the maximum tolerated single oral Compound A dose.

Bowel movement frequency was assessed during the 24 hour period after dosing for each dose-level group. Bowel movements were experienced in the placebo and in all active dose groups. There was a trend for increased bowel movements in subjects treated with Compound A as compared to those treated with placebo. The most striking effects were seen in subjects treated at the 96 µg dose level. Compared to only three of twelve subjects experiencing bowel movements in the placebo group, all six subjects in the 96 µg Compound A group experienced bowel movements. Furthermore, the average number of bowel movements per subject in this Compound A group (1.5) was three times greater than the average number of bowel movements per subject in the placebo group (0.5).

Multiple Rising Dose Study

Compound A was determined to be optimal when administered at the 24 µg dose TID and determined to be safe and tolerable up to 36 µg when administered TID for at least 6 days. The AEs that were experienced were those that were associated with the expected pharmacologic action of Compound A. However, given that the maximal total number of bowel movements was achieved at the 24 μg dose level, and that increasing doses were not associated with increased pharmacodynamic effects, but were associated with an increased AE profile, the 24 μg dose level was determined to be the best tolerated effective dose in healthy volunteers.

The volunteers experienced no SAEs. The main dose limiting side effect observed during the study was nausea. At the 24 μg dose level, one volunteer had three bouts of nausea and at the 30 μg dose level, two volunteers experienced a total of three bouts of nausea. At the 36 μg dose level, there was a notable increase in the incidence of nausea, with thirteen bouts of nausea being experienced by five out of six volunteers dosed at this level. Further to this, one volunteer at the 36 μg level experienced twelve episodes of diarrhea or loose stools, two episodes of nausea and three episodes of abdominal cramps during the dosing period. All vital signs and ECG measurements were normal throughout the study period and no central nervous system or physical abnormalities observed. The 36 μg dose level was determined to be the maximum tolerated multiple oral dose for the TID treatment regimen.

Bowel movement frequency was assessed in this study as well. As in the Phase I single rising dose study, the Compound A treatment groups exhibited more bowel movements than the placebo group. A total of 193 bowel movements were experienced in this study. Of these, 31 occurred in the placebo group, 70 in the 24 μg group, 51 in the 30 μg group and 41 in the 36 μg group.

Example 2

Phase II Dosage Studies

Eligible patients were treated with either placebo or total daily doses of 24 μg, 48 μg or 72 μg of Compound A for 21 days. One placebo or Compound A capsule was taken 3 times each day (AM, Noon, and PM). Compound A was administered as 24 μg oral capsules. Patients assigned to receive the total daily 24 μg Compound A dose took one Compound A capsule in the AM and one matching placebo capsule both at Noon and in the PM; patients assigned to receive the total daily 48 μg Compound A dose took one Compound A capsule in both the AM and PM and one matching placebo capsule at Noon; patients assigned to receive the total daily 72 μg Compound A dose took one Compound A capsule in the AM, at Noon, and in the PM.

Based on the overall efficacy results, doses of Compound A as low as 24 μg tended to relieve constipation, however, based on statistical analyses, the minimum effective dose of Compound A was 48 μg per day. Compared to placebo treatment, patients taking 48 μg or 72 μg of Compound A experienced statistically significant increases in the daily average number of spontaneous bowel movements at Week 1 and Week 2. Administration of 48 μg or 72 μg of Compound A produced a statistically significant increase in the proportion of patients who had a spontaneous bowel movement on Day 1. Statistically significant improvements in stool consistency were observed at all post-baseline time points in patients taking 48 μg and 72 μg of Compound A. Statistically significant improvements in constipation severity were observed at Week 3 in patients taking 48 μg of Compound A and at Weeks 2 and 3 in patients taking 72 μg of Compound A.

What is claimed is:

1. A dosage unit comprising a prostaglandin (PG) analog represented by Formula (I) and/or its tautomers, and a pharmaceutically suitable excipient, wherein the dosage unit contains said PG analog in an amount of 24 μg+/−10%:

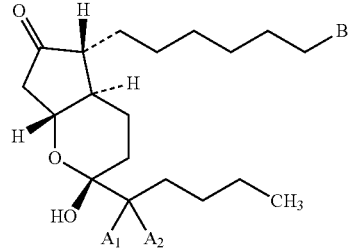

Formula (I)

where $A_1$ and $A_2$ are fluorine atoms and
B is —COOH, including its pharmaceutically acceptable salts, esters or amides.

2. The dosage unit of claim 1, wherein said PG analog is the monocyclic tautomer of formula (I).

3. The dosage unit of claim 1, wherein said PG analog is the bi-cyclic tautomer of formula (I).

4. The dosage unit of claim 1, wherein said pharmaceutically suitable excipient is orally acceptable.

5. The dosage unit of claim 1, wherein said pharmaceutically suitable excipient is a medium chain fatty acid.

6. The dosage unit of claim 1, wherein B is —COOH.

7. The dosage unit of claim 1, which is suitable for use in a human patient.

8. The dosage unit of claim 7, which is suitable for use in relieving or preventing constipation.

9. The dosage unit of claim 5, wherein B is —COOH.

10. The dosage unit of claim 1, wherein the PG analog is present in an amount of 24 μg.

11. The dosage unit of claim 10, wherein B is —COOH.

12. The dosage unit of claim 10, wherein said pharmaceutically suitable excipient is a medium chain fatty acid.

13. The dosage unit of claim 11, wherein said pharmaceutically suitable excipient is a medium chain fatty acid.

* * * * *